(12) United States Patent
Tayebi et al.

(10) Patent No.: US 11,338,067 B2
(45) Date of Patent: May 24, 2022

(54) SYNTHETIC PROSTHESIS FOR USE IN OSTEO-ODONTO-KERATOPROSTHESIS (OOKP) SURGERY

(71) Applicants: Marquette University, Milwaukee, WI (US); Christopher Swee Chau Liu, Hove (GB); Mehran Zarei Ghanavati, London (GB)

(72) Inventors: Lobat Tayebi, Milwaukee, WI (US); Morteza Rasoulianboroujeni, Milwaukee, WI (US); Christopher Swee Chau Liu, Hove (GB); Mehran Zarei Ghanavati, London (GB)

(73) Assignee: Marquette University, Milwaukee, WI (US)

( * ) Notice: Subject to any disclaimer, the term of this patent is extended or adjusted under 35 U.S.C. 154(b) by 19 days.

(21) Appl. No.: 16/497,904

(22) PCT Filed: Mar. 30, 2018

(86) PCT No.: PCT/US2018/025343
§ 371 (c)(1),
(2) Date: Sep. 26, 2019

(87) PCT Pub. No.: WO2018/183801
PCT Pub. Date: Oct. 4, 2018

(65) Prior Publication Data
US 2020/0023099 A1    Jan. 23, 2020

Related U.S. Application Data

(60) Provisional application No. 62/478,755, filed on Mar. 30, 2017.

(51) Int. Cl.
*A61L 27/56*    (2006.01)
*A61F 2/14*    (2006.01)
(Continued)

(52) U.S. Cl.
CPC ............... *A61L 27/56* (2013.01); *A61L 27/04* (2013.01); *A61L 27/10* (2013.01); *A61L 27/12* (2013.01);
(Continued)

(58) Field of Classification Search
CPC ...... A61F 2/142; A61F 2/1451; A61F 2/1453; A61L 2430/16; A61L 27/56
See application file for complete search history.

(56) References Cited

U.S. PATENT DOCUMENTS 5,843,185 A * 12/1998 Leon Rolden .......... A61L 27/22
                                                      623/5.11
2002/0165616 A1* 11/2002 Heide .................... A61L 27/56
                                                      623/23.56
(Continued)

FOREIGN PATENT DOCUMENTS

EP    1498087 A2    1/2005
RU    2139014 A1    10/1999
(Continued)

OTHER PUBLICATIONS

Cox, N. H., et al. "Blindness due to the IgA variant of epidermolysis bullosa acquisita, and treatment with osteo-odonto-keratoprosthesis." British Journal of Dermatology 156.4 (2007): 775-777.
(Continued)

*Primary Examiner* — Javier G Blanco
(74) *Attorney, Agent, or Firm* — Quarles & Brady LLP

(57) ABSTRACT

Disclosed herein is a prosthesis that may be used to replace standard prosthetic material used in osteo-odonto-keratoprosthesis (OOKP) surgery. The disclosed prosthesis is not prepared from tissue removed from a patient's tooth and jaw bone, but rather is a synthetic prosthesis. The synthetic prosthesis typically includes a solid part for supporting an
(Continued)

optical cylinder and a porous part that facilitates bio-integration of the implanted prosthesis into the patient's eye.

16 Claims, 18 Drawing Sheets

(51) Int. Cl.
*A61L 27/04* (2006.01)
*A61L 27/10* (2006.01)
*A61L 27/12* (2006.01)
*A61L 27/18* (2006.01)
*A61L 27/40* (2006.01)

(52) U.S. Cl.
CPC ............... *A61L 27/18* (2013.01); *A61L 27/40* (2013.01); *A61F 2/142* (2013.01); *A61F 2/1451* (2015.04); *A61F 2/1453* (2015.04); *A61L 2430/16* (2013.01)

(56) References Cited

U.S. PATENT DOCUMENTS

| | | |
|---|---|---|
| 2010/0080840 A1 | 4/2010 | Cho |
| 2015/0216651 A1* | 8/2015 | Parel ............... A61F 2/142 623/5.11 |
| 2016/0144069 A1 | 5/2016 | Cho |
| 2018/0049878 A1* | 2/2018 | Stulberg ............ A61F 2/389 |
| 2018/0250239 A1* | 9/2018 | Ilios ............... A61K 9/7007 |

FOREIGN PATENT DOCUMENTS

| | | | |
|---|---|---|---|
| RU | 2367379 C1 | 9/2009 | |
| WO | WO-0239930 A1 * | 5/2002 | ............ A61L 27/44 |
| WO | 2014039495 A1 | 3/2014 | |

OTHER PUBLICATIONS

Dong, Y., et al. "An improved biofunction of titanium for keratoprosthesis by hydroxyapatite-coating." Journal of biomaterials applications 28.7 (2014): 990-997.

European Patent Office. Extended European Search Report for application 18775701.8, dated Oct. 23, 2020. 8 pages.

Fong, K. C. S., et al. "Imaging of osteo-odonto-keratoprosthesis by electron beam tomography." British journal of ophthalmology 89.8 (2005): 956-959.

Intellectual Property Office of Singapore. Search Report and Written Opinion for application 11201908883R, dated Dec. 24, 2020. 8 pages.

International Searching Authority. International Search Report and Written Opinion for application PCT/US2018/025343, dated Aug. 2, 2018. 7 pages.

Liu C, et al. The osteo-odonto-keratoprosthesis (OOKP). Seminars in ophthalmology: Taylor & Francis; 2005. p. 113-128.

Strampelli B. Keratoprosthesis with osteodontal tissue. Am J Ophthalmol 1963;89:39.

* cited by examiner

SYNTHETIC PROSTHESIS FOR USE IN OSTEO-ODONTO-KERATOPROSTHESIS (OOKP) SURGERY

CROSS-REFERENCE TO RELATED PATENT APPLICATIONS

The present application represents the U.S. national stage entry of International Application No. PCT/US2018/025343 filed Mar. 30, 2018, which application claims the benefit of priority under 35 U.S.C. § 119(e) to U.S. Provisional Application No. 62/478,755, filed on Mar. 30, 2017, the content of which is incorporated herein by reference in its entirety.

BACKGROUND

The field of the invention relates to materials for use in eye surgery. In particular, the field of the invention relates to synthetic prosthetic materials that may be used to replace standard prosthetic materials used in performing osteo-odonto-keratoprosthesis (OOKP) surgery.

Osteo-odonto-keratoprosthesis (OOKP) surgery, otherwise referred to as "tooth in eye" surgery is a technique developed in the early 1960s by Strampelli to replace damaged cornea in blind patients [1]. The technique is used when a cadaveric corneal transplant is likely to fail. In OOKP, a synthetic corneal transplant is created using the root of a tooth, the underlying alveolar bone of the tooth, and a plastic optical cylinder made of poly(methyl methacrylate) (PMMA). OOKP is now widely recognized by corneal surgeons worldwide as one of the top treatment choices for patients with end stage inflammatory corneal disease. For instance, almost no other device or technique works as satisfactory as OOKP for a dry eye [2].

OOKP surgery is usually carried out in two stages. In Stage 1, a monoradicular tooth and surrounding jaw bone are collected from the patient to prepare an osteo-odonto-lamina. The tooth root and adjacent jaw bone are cut sagittally and then removed by slicing across the bridging bone. Pulp is exposed and removed. The crown of the tooth then is cut laterally. A hole then is drilled through the dentine of the tooth. A PMMA optical cylinder is fitted through the anterior of the hole and is cemented in place to prepare the prosthesis. The prosthesis is then implanted into a submuscular pouch often created by making a slit in the lower eye lid of the patient's fellow eye or in the patient's cheek and left over there for a period of 2-4 months in order for the tissue surrounding the prosthesis to become vascularized prior to Stage 2.

Prior to Stage 2, the corneal surface of the eye is prepared to receive a buccal mucous membrane graft removed from the patient. The buccal mucous membrane graft placed over the corneal surface of the eye becomes vascularized prior to Stage 2 surgery and subsequently will provide the blood supply to the bone part of the prosthesis.

At Stage 2, the prosthesis is removed from the submuscular pouch. All the blood vessels that have grown over the surface of the PMMA optical cylinder are then detached. The buccal mucous membrane graft placed over the corneal surface then is slit and peeled back. A hole is made in the patient's eye and the contents of the eye are removed. The prosthesis then is inserted into the eye and allowed to heal [2]. The PMMA optical cylinder allows light to enter the patient's eye and provides vision.

Even though the OOKP is a very useful and efficient technique, it is very aggressive. An OOKP patient requires at least two surgeries and the patient loses his/her tooth. Therefore, new techniques and keratoprostheses are desirable in order to replace standard techniques and prostheses used in sOOKP. Here, the present inventors disclose a synthetic prosthesis for use in OOKP that may replace the standard prosthesis that is prepared from a patient's tooth and jaw bone in OOKP.

SUMMARY

Disclosed herein is a prosthesis that may be used to replace standard prosthetic material used in osteo-odonto-keratoprosthesis (OOKP) surgery. The disclosed prosthesis is not prepared from tissue removed from a patient's tooth and jaw bone, but rather is a synthetic prosthesis. The synthetic prosthesis typically includes a solid part for supporting an optical cylinder and a porous part that facilitates bio-integration of the implanted prosthesis into the patient's eye.

DETAILED DESCRIPTION

Figure 1:
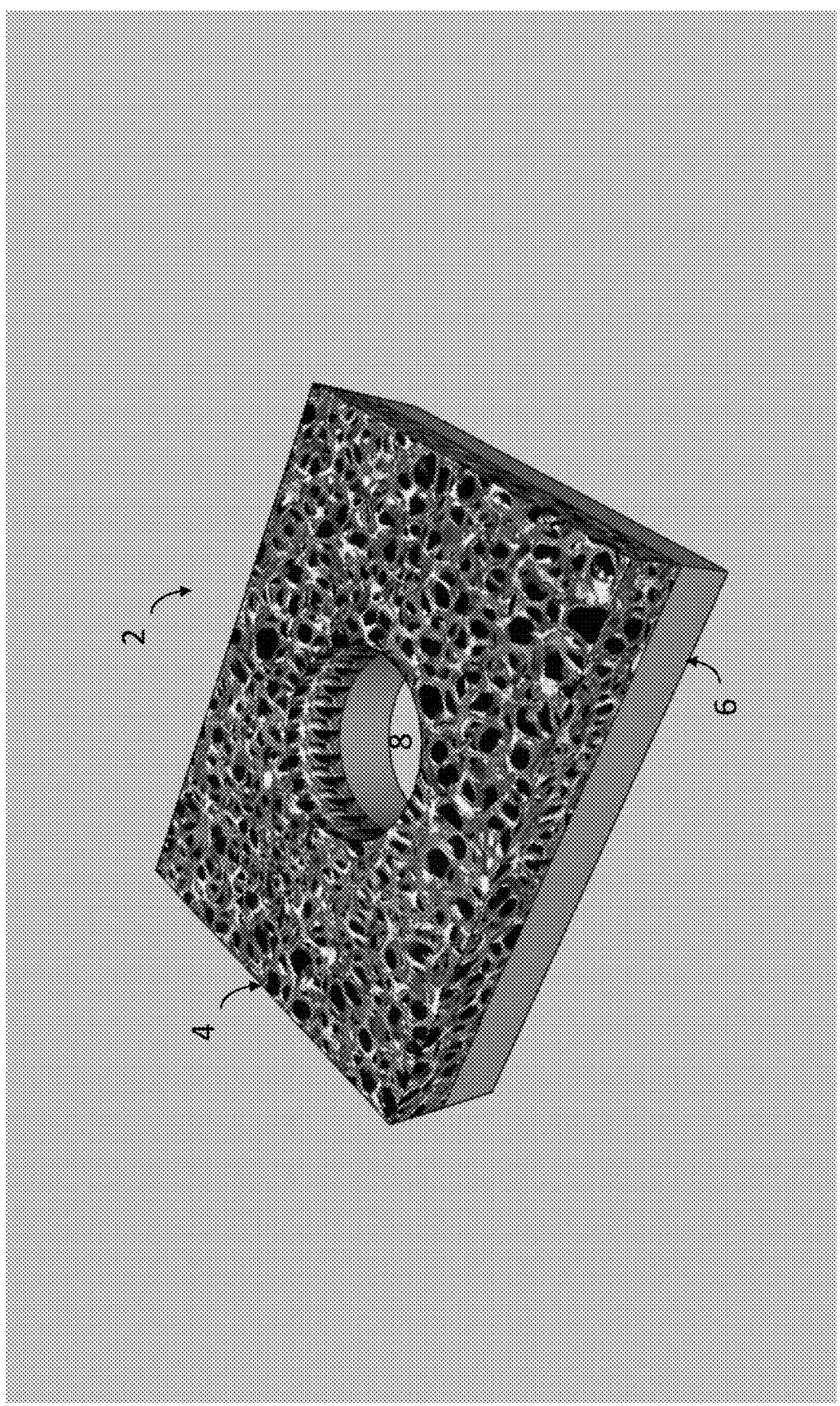
FIG. 1. Schematic representation of one embodiment of a synthetic prosthesis as contemplated herein.

The disclosed subject matter further may be described utilizing terms as defined below.

Unless otherwise specified or indicated by context, the terms "a", "an", and "the" mean "one or more." For example, "a prosthesis" should be interpreted to mean "one or more prostheses."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The disclosed prosthesis may be utilized in keratoprosthesis surgery to replace standard prosthetic material utilized in osteo-odonto-keratoprosthesis (OOKP) surgery such as modified dental material such as a tooth. In particular, the disclosed prosthesis may be utilized to support and/or hold an optical cylinder used as a cornea replacement. As such, the disclosed prosthesis may be used to replace the standard modified dental material commonly used in osteo-odonto-keratoprosthesis (OOKP) surgery to support and/or hold an optical cylinder.

ILLUSTRATIVE EMBODIMENTS

The following embodiments are illustrative and should not be interpreted to limit the scope of the claimed subject matter.

Embodiment 1

A synthetic prosthesis for use in eye surgery, the synthetic prosthesis comprising a porous part and a solid part and a hole through the porous part and the solid part.

Embodiment 2

The synthetic prosthesis of embodiment 1, wherein the synthetic prosthesis is configured for use in keratoprosthesis surgery such as a replacement for standard prosthetic materials such as a modified dental material used in performing osteo-odonto-keratoprosthesis (OOKP) surgery.

Embodiment 3

The synthetic prosthesis of embodiment 1 or 2, wherein the porous part and solid part are laminate parts.

Embodiment 4

The synthetic prosthesis of embodiment 1 or 2, wherein the porous part and solid part of the synthetic prosthesis are permanently attached.

Embodiment 5

The synthetic prosthesis of embodiment 1 or 2, wherein the porous part and solid part of the synthetic prosthesis are removably attached.

Embodiment 6

The synthetic prosthesis of any of the foregoing embodiments, wherein the porous part and the solid part comprise or consist of the same material.

Embodiment 7

The synthetic prosthesis of any of the foregoing embodiments, wherein the porous part and the solid part comprise or consist of different materials.

Embodiment 8

The synthetic prosthesis of any of the foregoing embodiments, wherein the porous part and the solid part comprise or consist of the same material or different materials selected from metal material (e.g., metal or metal alloy), ceramic material (e.g., hydroxyapatite, tri-calcium phosphate), polymeric material (e.g., poly(methyl methacrylate) (PMMA) or polyethylene), or a composite comprising any combination of metal material, ceramic material, and polymeric material.

Embodiment 9

The synthetic prosthesis of any of the foregoing embodiments, wherein the porous part and the solid part can be coated using the same material or different materials selected from metal material (e.g., metal or metal alloy), ceramic material (e.g., hydroxyapatite, tri-calcium phosphate), polymeric material (e.g., poly(methyl methacrylate) (PMMA) or polyethylene), hydrogel materials, or a composite comprising any combination of metal material, ceramic material, hydrogel materials, and polymeric material.

Embodiment 10

The synthetic prosthesis of any of the foregoing embodiments, wherein the dimensions of the porous part and the solid part are the same or different.

Embodiment 11

The synthetic prosthesis of any of the foregoing embodiments, wherein the dimensions of the porous part and the solid part are different.

Embodiment 12

The synthetic prosthesis of any of the foregoing embodiments, wherein the Width (W) of the porous part ranges from 2 to 20 mm, preferably 6-16 mm, and more preferably 10-12 mm.

Embodiment 13

The synthetic prosthesis of any of the foregoing embodiments, wherein the Depth (D) of the porous part ranges from 1 to 15 mm, preferably 4-12 mm, more preferably 7-9 mm.

Embodiment 14

The synthetic prosthesis of any of the foregoing embodiments, wherein the Height (H) of the porous part ranges from 0.1 to 5 mm, preferably 0.5-2.5 mm, more preferably 1-2 mm.

Embodiment 15

The synthetic prosthesis of any of the foregoing embodiments, wherein the width (W) of the solid part ranges from 2 to 20 mm, preferably 6-16 mm, more preferably 10-12 mm.

Embodiment 16

The synthetic prosthesis of any of the foregoing embodiments, wherein the Depth (D) of the solid part ranges from 1 to 15 mm, preferably 4-12 mm, more preferably 7-9 mm.

Embodiment 17

The synthetic prosthesis of any of the foregoing embodiments, wherein the Height (H) of the solid part ranges from 0.1 to 5 mm, preferably 0.25-2 mm, more preferably 0.5-1.5 mm.

Embodiment 18

The synthetic prosthesis of any of the foregoing embodiments, wherein the porous part comprises or is made of metal material (e.g., titanium or titanium alloy such as Ti-6Al-4V alloy).

Embodiment 19

The synthetic prosthesis of any of the foregoing embodiments, wherein the porous part comprises or is made of ceramic material (e.g., hydroxyapatite, tri-calcium phosphate).

Embodiment 20

The synthetic prosthesis of any of the foregoing embodiments, wherein the porous part comprises or is made of a polymeric material (e.g., poly(methyl methacrylate) (PMMA) and/or polyethylene material).

Embodiment 21

The synthetic prosthesis of any of the foregoing embodiments, wherein the porous part comprises or is made of a composite comprising a combination of any of metal material, ceramic material, and/or polymeric material.

Embodiment 22

The synthetic prosthesis of any of the foregoing embodiments, wherein the porous part may be coated using any of metal material, ceramic material, polymeric material and/or a composite comprising a combination of any of metal material, ceramic material, and/or polymeric material.

Embodiment 23

The synthetic prosthesis of any of the foregoing embodiments, wherein the porous part comprises pores having an average effective pore size of 10 to 1000 microns, preferably 100 to 800 microns, more preferably 200-600 microns.

Embodiment 24

The synthetic prosthesis of any of the foregoing embodiments, wherein the porous part has a volumetric porosity of 10 to 95%, preferably 20-80%, more preferably 45-75%.

Embodiment 25

The synthetic prosthesis of any of the foregoing embodiments, wherein the porous part facilitates bio-integration of the prosthesis (e.g., into an eye of a patient).

Embodiment 26

The synthetic prosthesis of any of the foregoing embodiments, wherein the solid part comprises or is made of metal material (e.g., titanium or titanium alloy such as Ti-6Al-4V alloy).

Embodiment 27

The synthetic prosthesis of any of the foregoing embodiments, wherein the solid part comprises or is made of ceramic material (e.g., hydroxyapatite, tri-calcium phosphate).

Embodiment 28

The synthetic prosthesis of any of the foregoing embodiments, wherein the solid part comprises or is made of a polymeric material (e.g., poly(methyl methacrylate) (PMMA) and/or polyethylene material).

Embodiment 29

The synthetic prosthesis of any of the foregoing embodiments, wherein the solid part comprises or is made of a composite comprising a combination of any of metal material, ceramic material, and/or polymeric material.

Embodiment 30

The synthetic prosthesis of any of the foregoing embodiments, wherein the solid part may be coated using any of metal material, ceramic material, polymeric material and/or a composite comprising a combination of any of metal material, ceramic material, and/or polymeric material.

Embodiment 31

The synthetic prosthesis of any of the foregoing embodiments, wherein the diameter of the hole through the prosthesis has a diameter that is the same through the porous part as through the solid part.

Embodiment 32

The synthetic prosthesis of any of the foregoing embodiments, wherein the diameter of the hole through the prosthesis has a diameter that is different through the porous part than through the solid part.

Embodiment 33

The synthetic prosthesis of any of the foregoing embodiments, wherein the hole has a diameter from 1 to 8 mm, preferably 2-6 mm, more preferably 3-5 mm.

Embodiment 34

The synthetic prosthesis of any of the foregoing embodiments, wherein the hole is substantially centered in the prosthesis through the porous part and the solid part.

Embodiment 35

The synthetic prosthesis of any of the foregoing embodiments, wherein the hole deviates from the center of the porous part and/or the solid part.

Embodiment 36

The synthetic prosthesis of any of the foregoing embodiments further comprising an optical cylinder placed in the hole of the synthetic prosthesis (e.g., wherein the optical cylinder comprises clear polymeric material with tissue tolerance and optical properties such as poly(methyl methacrylate) (PMMA) and/or polyethylene material).

Embodiment 37

The synthetic prosthesis of any of the foregoing embodiment wherein the porous part is prepared by a method selected from replica template/replication, 3D-printing, microsphere sintering, particle sintering, powder sintering, fiber sintering, gas injection into the metal melt, decomposition of foaming agents, plasma spraying, space holder method, combustion synthesis, vapor deposition, and electro discharge compaction.

Embodiment 38

A method for performing eye surgery (e.g. keratoprosthesis surgery), the method comprising inserting the synthetic prosthesis of any of the foregoing embodiments into an eye of a patient.

Embodiment 39

The method of embodiment 38, wherein prior to inserting the synthetic prosthesis into the eye of a patient, the synthetic prosthesis is placed into a submuscular pouch of the patient and is allowed to vascularize.

EXAMPLES

The following examples are illustrative and are not intended to limit the scope of the claimed subject matter.

Example 1—Synthetic Prosthesis for Use in Osteo-Odonto-Keratoprosthesis (OOKP) Surgery as Replacement for Dental Material The disclosed synthetic prosthetic devices may be used as a replacement for dental material in osteo-odonto-keratoprosthesis (OOKP) surgery. In OOKP surgery, dental material (e.g., a tooth) is configured to support an optical cylinder which is transplanted to a patient's eye to replace a diseased or defective cornea. As such, in OOKP surgery, the patient loses a tooth. The disclosed synthetic prosthetic devices may be used as a replacement in OOKP surgery to provide a support for an optical cylinder (e.g., via a solid part) and to provide material for integrating the prosthetic device into the eye of the patient (e.g., via a porous part).

Figure 2:
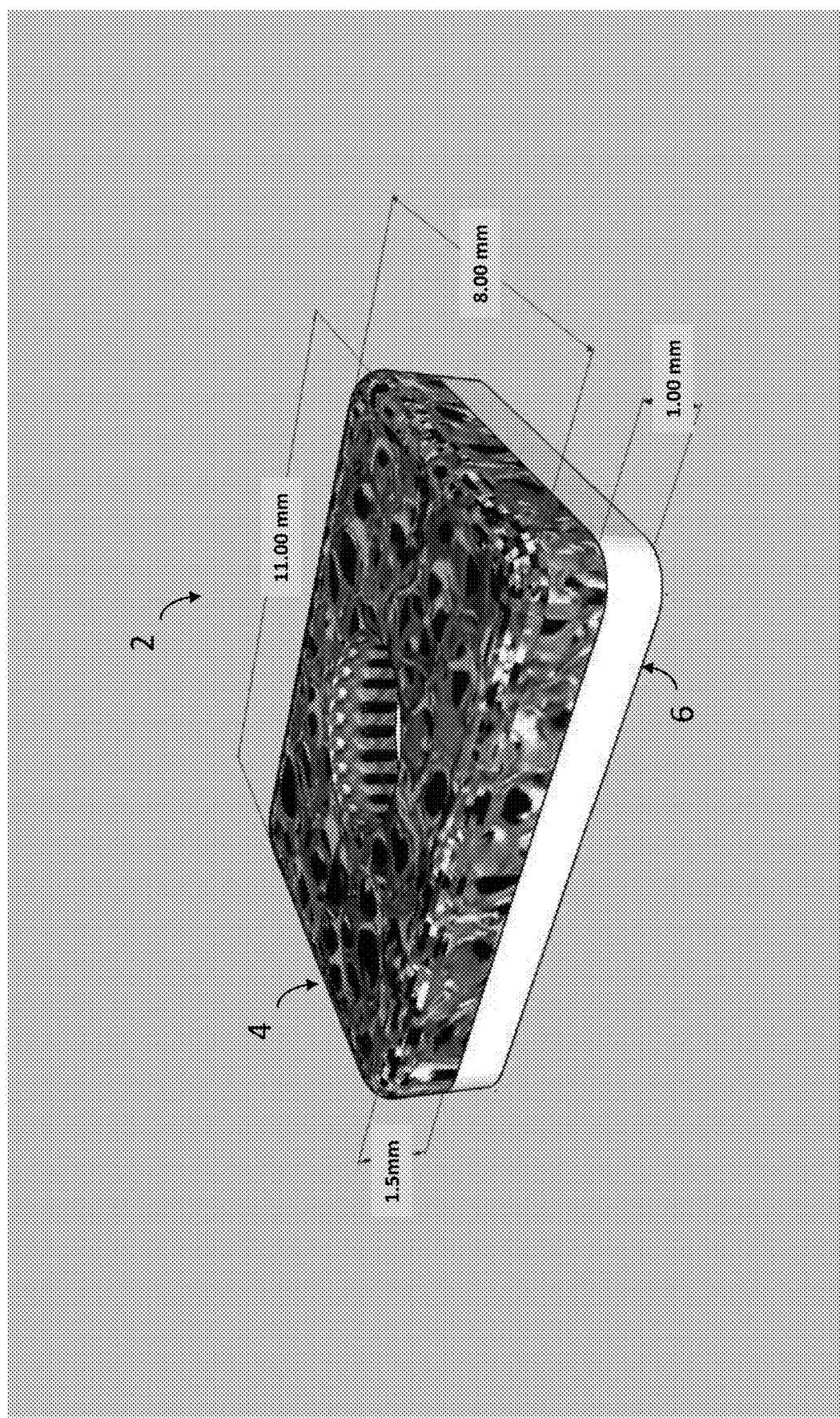
FIG. 2. Schematic representation of one embodiment of a synthetic prosthesis as contemplated herein including exemplary dimension sizes.
Figure 3:
FIG. 3. Photograph of one exemplary prototype of a synthetic prosthesis as contemplated herein illustrating the solid part on the top and the porous part on the bottom.
Figure 4:
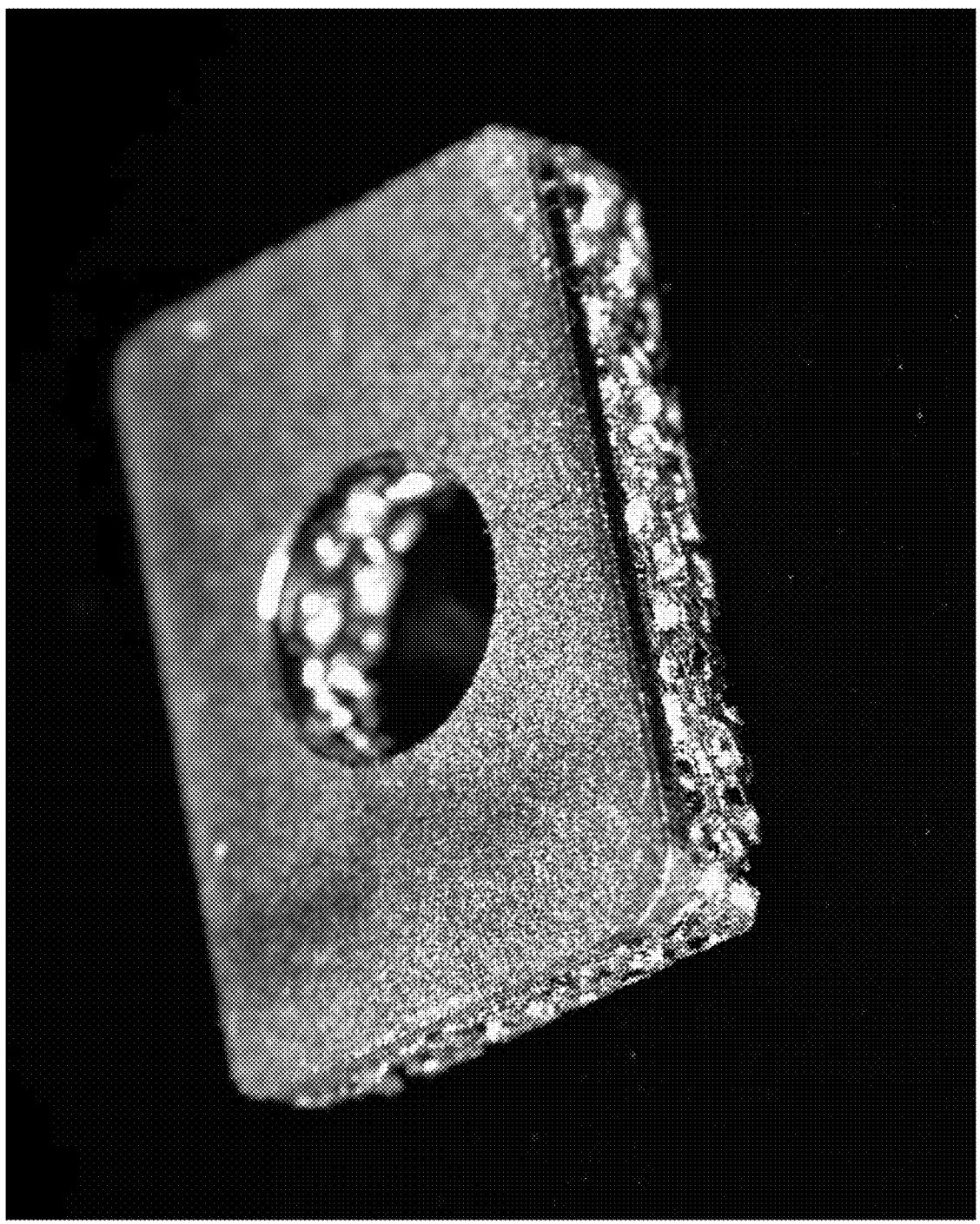
FIG. 4. Another photograph of one exemplary prototype of a synthetic prosthesis as contemplated herein illustrating the solid part on the top and the porous part on the bottom.
Figure 5:
FIG. 5. Another photograph of one exemplary prototype of a synthetic prosthesis as contemplated herein illustrating the solid part on the top and the porous part on the bottom.
Figure 6:
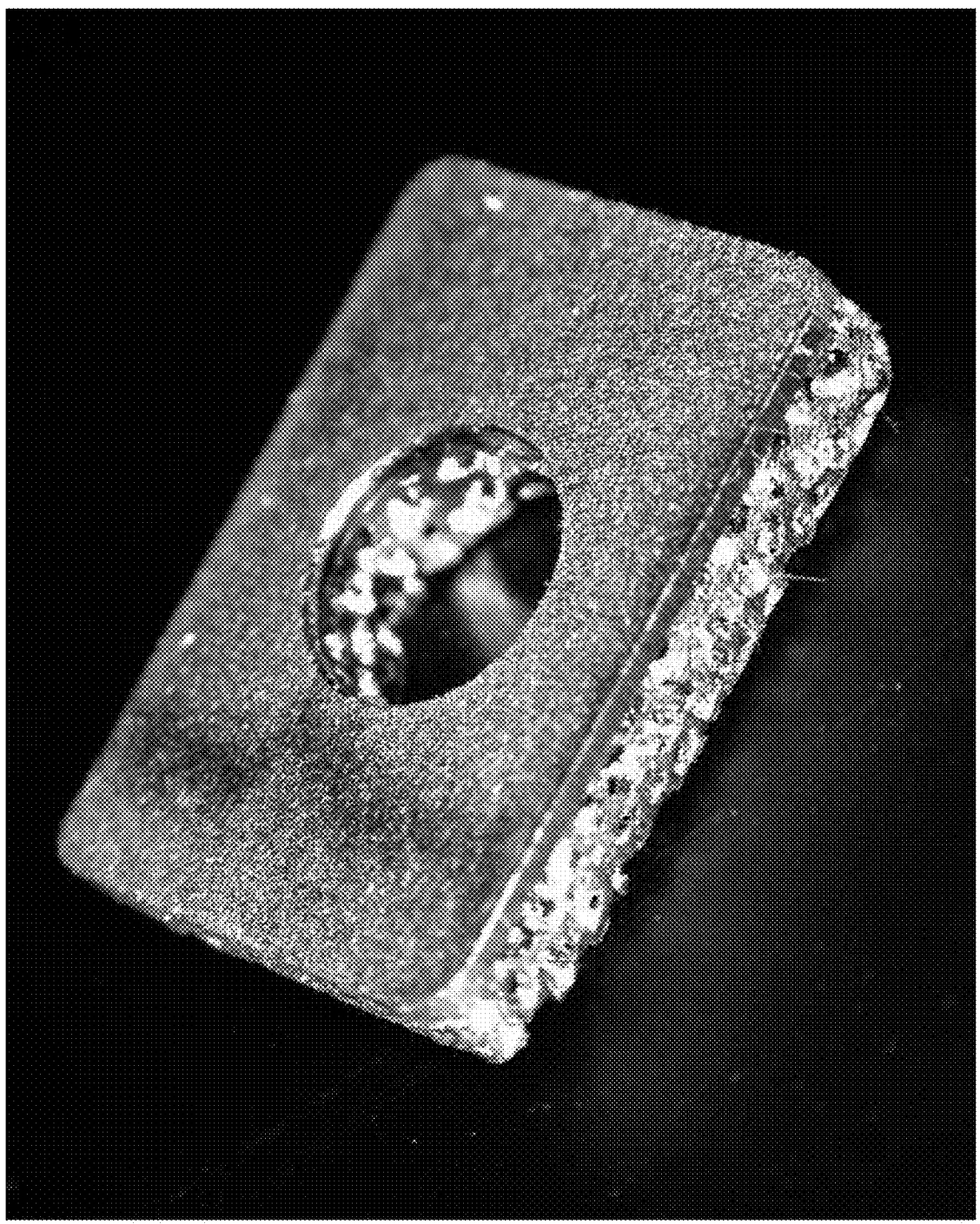
FIG. 6. Another photograph of one exemplary prototype of a synthetic prosthesis as contemplated herein illustrating the solid part on the top and the porous part on the bottom.
Figure 7:
FIG. 7. Photograph of one exemplary prototype of a synthetic prosthesis as contemplated herein illustrating the porous part on the top and the solid part on the bottom.
Figure 8:
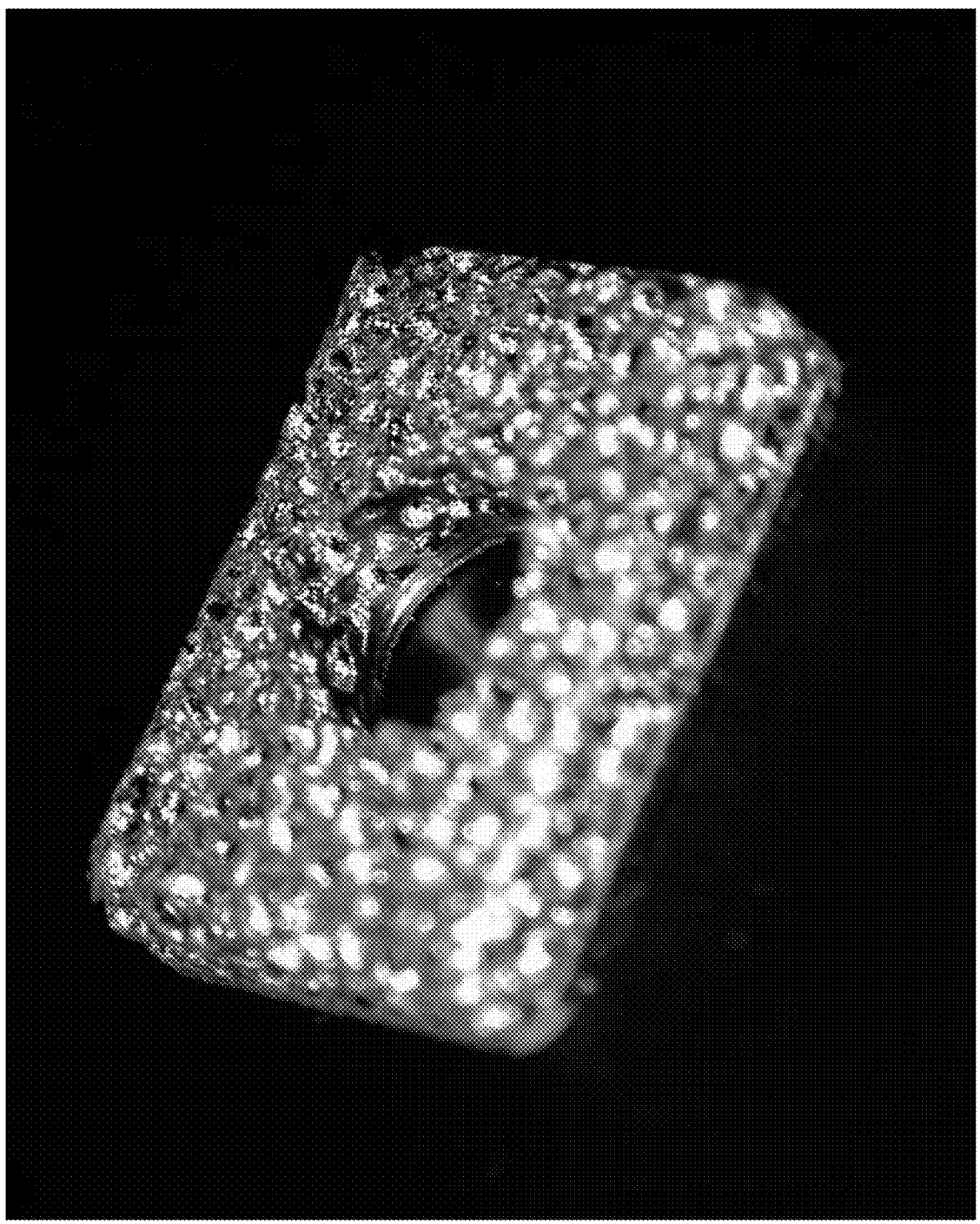
FIG. 8. Another photograph of one exemplary prototype of a synthetic prosthesis as contemplated herein illustrating the porous part on the top and the solid part on the bottom.
Figure 9:
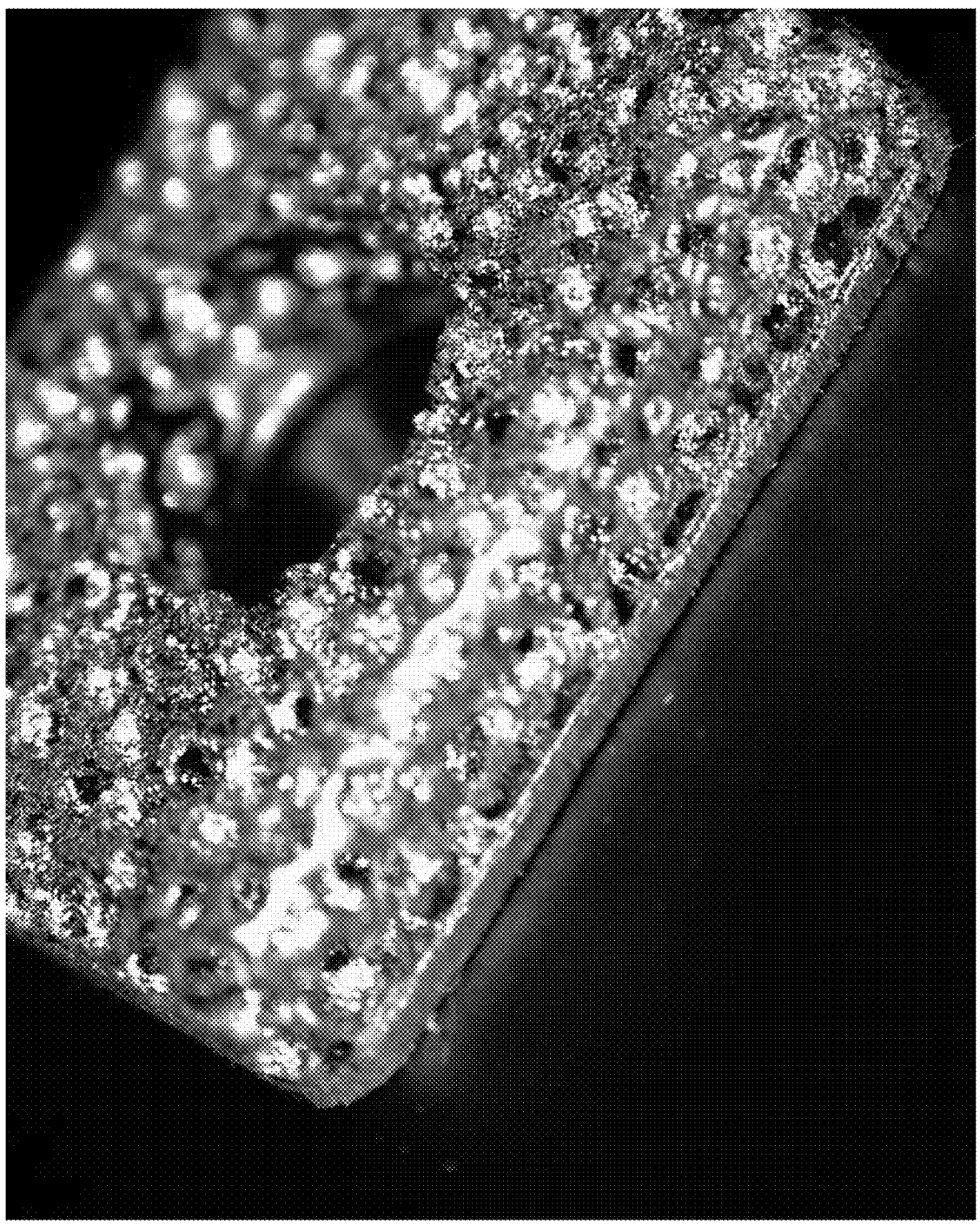
FIG. 9. Another photograph of one exemplary prototype of a synthetic prosthesis as contemplated herein illustrating the porous part on the top and the solid part on the bottom.
Figure 10:
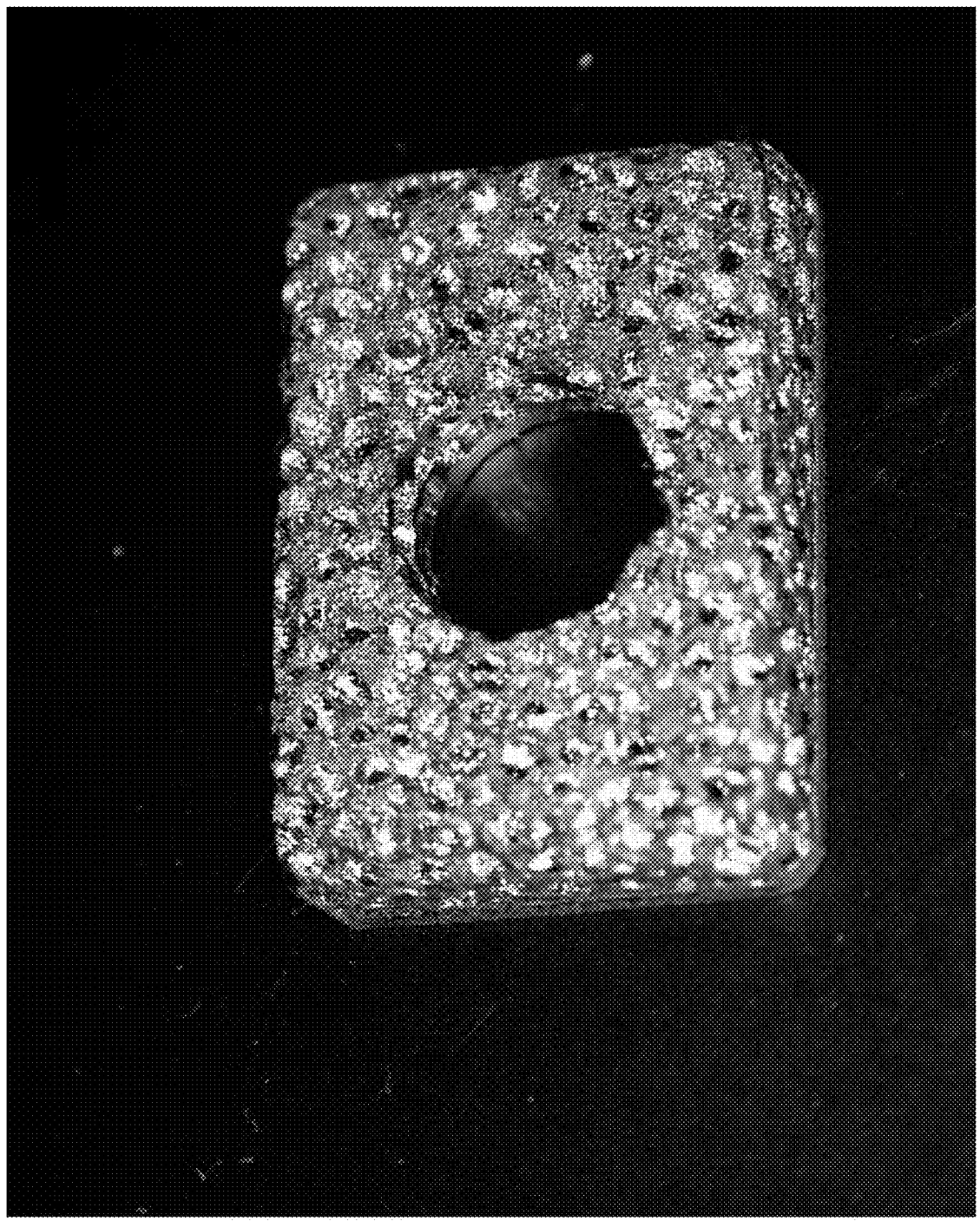
FIG. 10. Another photograph of one exemplary prototype of a synthetic prosthesis as contemplated herein illustrating the porous part on the top and the solid part on the bottom.
Figure 11:
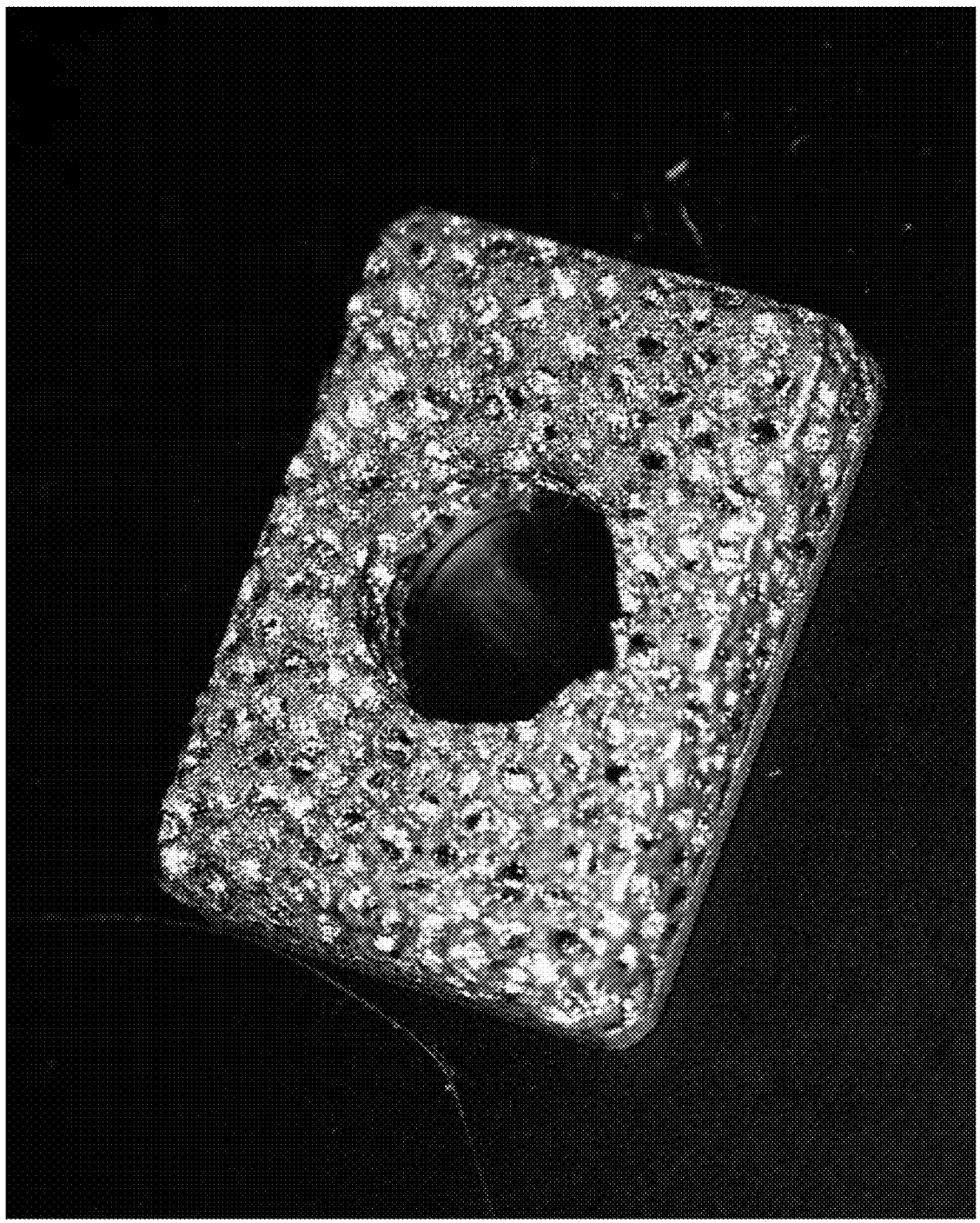
FIG. 11. Another photograph of one exemplary prototype of a synthetic prosthesis as contemplated herein illustrating the porous part on the top and the solid part on the bottom.
Figure 12:
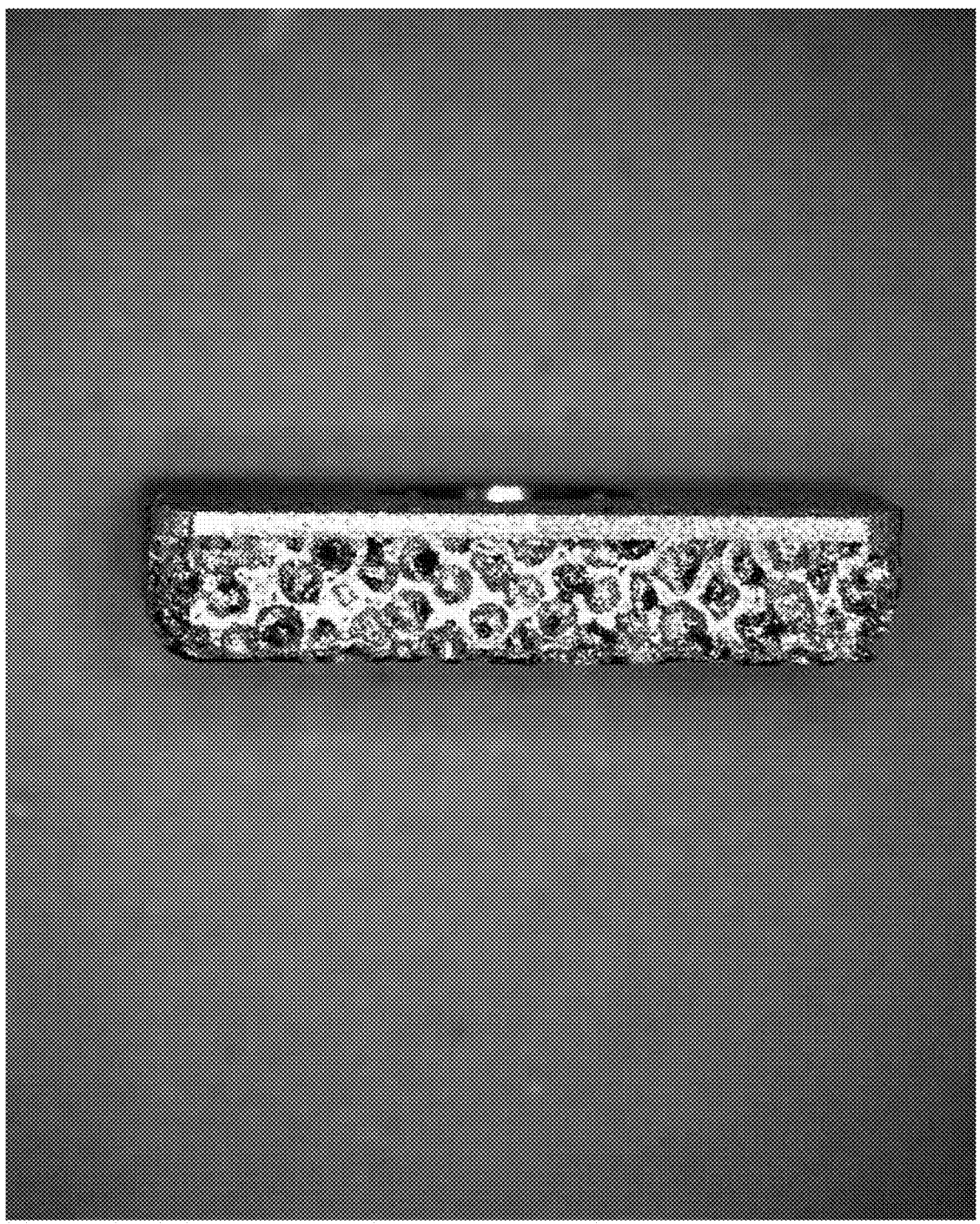
FIG. 12. Photograph of one exemplary prototype of a synthetic prosthesis as contemplated herein illustrating providing a side view with the solid part on the right and the porous part on the left.
Figure 13:
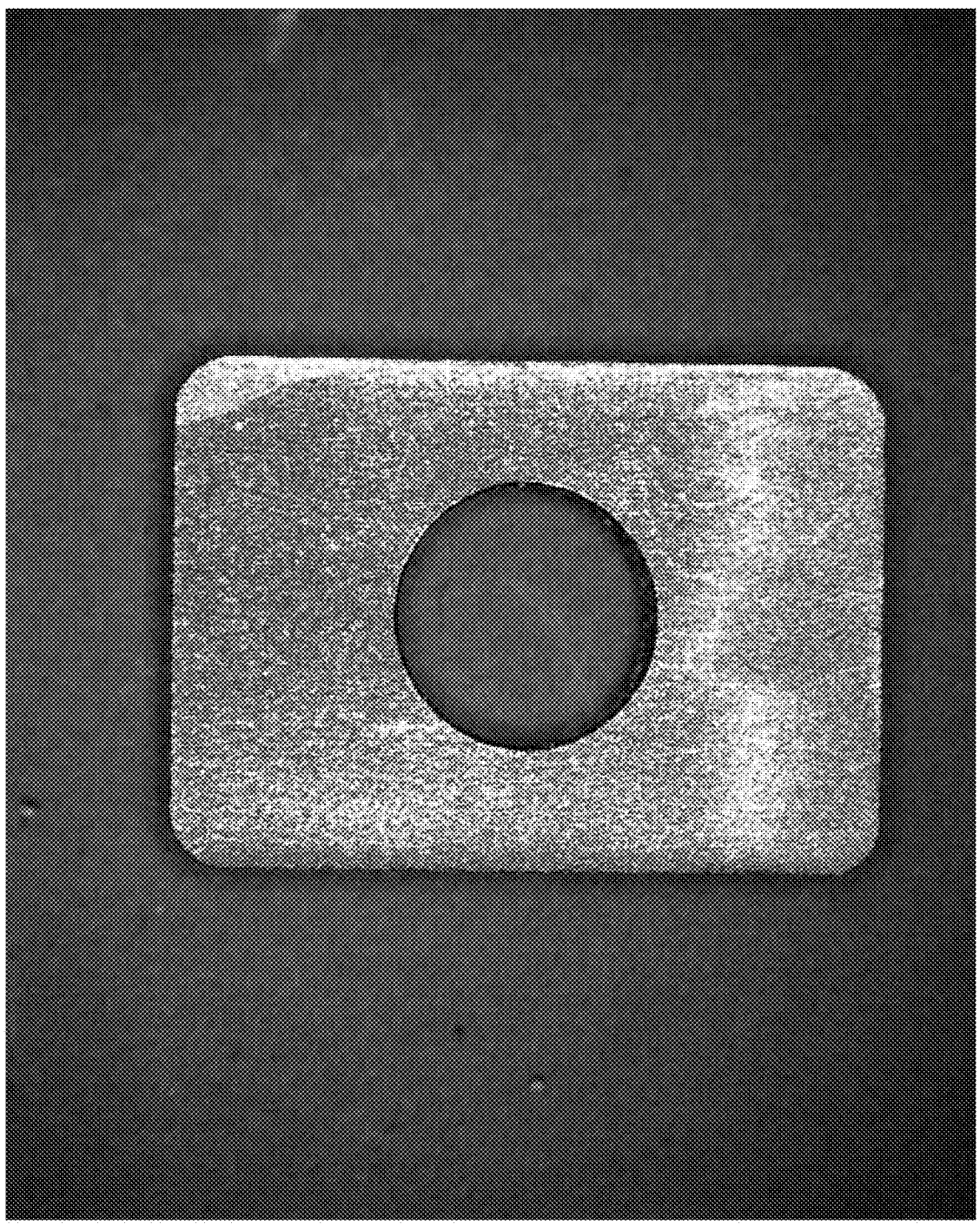
FIG. 13. Photograph of one exemplary prototype of a synthetic prosthesis as contemplated herein illustrating providing a top view of the solid part.
Figure 14:
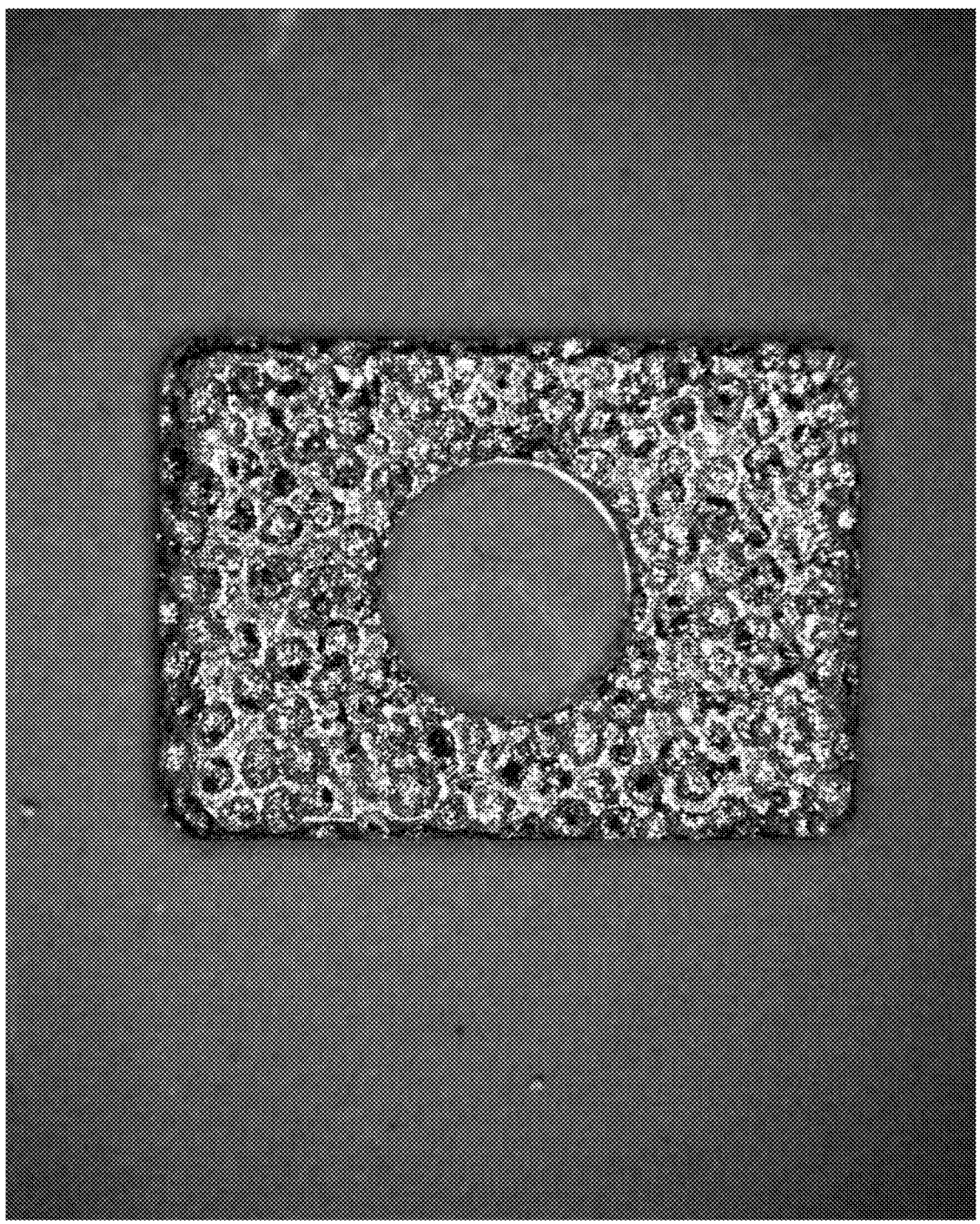
FIG. 14. Photograph of one exemplary prototype of a synthetic prosthesis as contemplated herein illustrating providing a top view of the porous part.

Exemplary synthetic prosthesis 2 are illustrated in FIGS. 1 and 2. The synthetic prostheses of FIG. 1 and FIG. 2 include at least two laminate parts: a porous part 4 and a solid part 6. The synthetic prosthesis has a hole 8 in the middle for receiving an optical cylinder. Photographs of exemplary prototypes of a synthetic prosthetic device as contemplated herein are provided in FIGS. 3-14.

As contemplated, the disclosed synthetic prosthesis may have one or more of the following features:

The synthetic prosthesis may comprise or consist of at least two parts: a porous part, and a solid part.

In some embodiments, the synthetic prosthesis is formed from a single material (i.e., the synthetic prosthesis is monolithic) and the synthetic prosthesis is manufactured to have a porous part (or portion) and a solid part (or portion), for example in a single-step manufacturing procedure. In other embodiments, the synthetic prosthesis is formed from two or more materials which may be the same or different materials. The two or more materials form the porous part and the solid part. In some embodiments, the synthetic prosthesis is formed from a separate porous part and a separate solid part.

In embodiments where the synthetic prosthesis is formed from a separate porous part and a separate solid part, the porous part and solid part of the synthetic prosthesis may be permanently or removably attached. In some embodiments, the porous part and the solid part are permanently attached (e.g., via application of an adhesive material and/or via a sintering process). The porous part and the solid part may be used together or may be removably attached and used separately. In particular, the synthetic prosthesis may be formed from a separate laminate porous part and a separate solid laminate part, which separate laminate porous part and a separate solid laminate part may be formed from the same or different material and which separate laminate porous part and a separate solid laminate part may be permanently or removable attached.

The porous part and solid part may comprise or consist of the same material or different materials. The porous part and solid part may be manufactured similarly or differently using the same material or different materials. Whether the same or different materials are used to manufacture the porous part and the solid part, in some embodiments of the disclosed synthetic prosthesis the material(s) of the porous part and/or solid part may be metal, ceramic, polymer, or a composite comprising any combination of metal, ceramic, and polymer.

The dimensions of the porous part and the solid part may be the same or different. In some embodiments, the Width (W) of the porous part ranges from 2 to 20 mm, preferably 6-16 mm, and more preferably 10-12 mm. In some embodiments, the Depth (D) of the porous part ranges from 1 to 15 mm, preferably 4-12 mm, more preferably 7-9 mm. In some embodiments, the Height (H) of the porous part ranges from 0.1 to 5 mm, preferably 0.5-2.5 mm, more preferably 1-2 mm. In some embodiments, the width (W) of the solid part ranges from 2 to 20 mm, preferably 6-16 mm, more preferably 10-12 mm. In some embodiments, the Depth (D) of the solid part ranges from 1 to 15 mm, preferably 4-12 mm, more preferably 7-9 mm. In some embodiments, the Height (H) of the solid part ranges from 0.1 to 5 mm, preferably 0.25-2 mm, more preferably 0.5-1.5 mm.

In order to facilitate biointegration and or incorporation of the synthetic prosthesis into relevant biological tissues (e.g., during a keratoprosthesis procedure), the edges of the porous part of the synthetic prosthesis may be relatively smooth and rounded (i.e., not a sharp 90 degree angle), whereas the edges of the solid part of the synthesis may be sharper (e.g., approximating a sharp 90 degree angle). (See contrast between the synthetic prosthesis of FIG. 1 with the synthetic prosthesis of FIG. 2 and FIG. 12, also FIGS. 3-11).

In some embodiments of the disclosed synthetic prosthesis, the porous part may comprise or may be made of metals. In particular, the porous part may comprise or may be made of titanium or titanium alloys (e.g., Ti-6Al-4V alloy).

In some embodiments of the disclosed synthetic prosthesis, the porous part may comprise or may be made of ceramics. In particular, the porous part may comprise or made be made of hydroxyapatite, tri-calcium phosphate.

In some embodiments of the disclosed synthetic prosthesis, the porous part may comprise or may be made of a polymeric material. In particular, the porous part may comprise or may be made of poly(methyl methacrylate) (PMMA) and/or polyethylene material.

In some embodiments of the disclosed synthetic prosthesis, the porous part may comprise or may be made of a composite comprising a combination of any of metal (or metal alloy) material, ceramic material, and/or polymeric material as contemplated herein.

In some embodiments of the disclosed synthetic prosthesis, the porous part may be coated or treated using any of metal (or metal alloy) material, ceramic material, polymeric material, hydrogel materials, and/or a composite comprising a combination of any of metal (or metal alloy) material, ceramic material, hydrogel materials, and/or polymeric material as contemplated herein.

In some embodiments of the disclosed synthetic prosthesis, the porous part comprises pores having an average effective pore size of 10 to 1000 microns, preferably 100 to 800 microns, more preferably 200-600 microns.

In some embodiments of the disclosed synthetic prosthesis, the porous part has a volumetric porosity of 5 to 95%, preferably 10-90%, more preferably 20-80%, even more preferably 45-75% (or a porosity within a range bounded by any of these percentage values, e.g., 20-75%).

Figure 15:
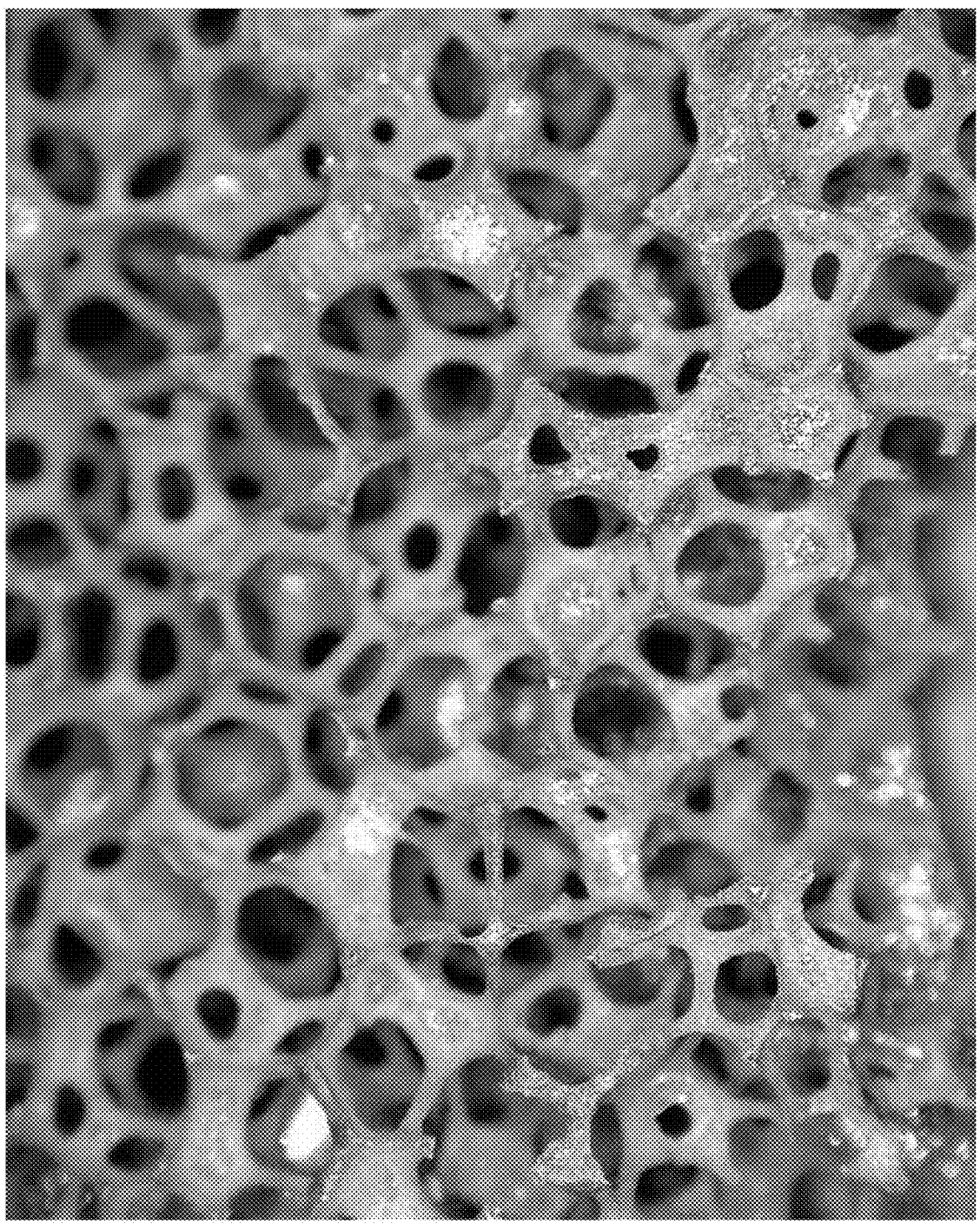
FIG. 15. Photograph of one embodiment of a porous part prepared by replica template/replication.
Figure 16:
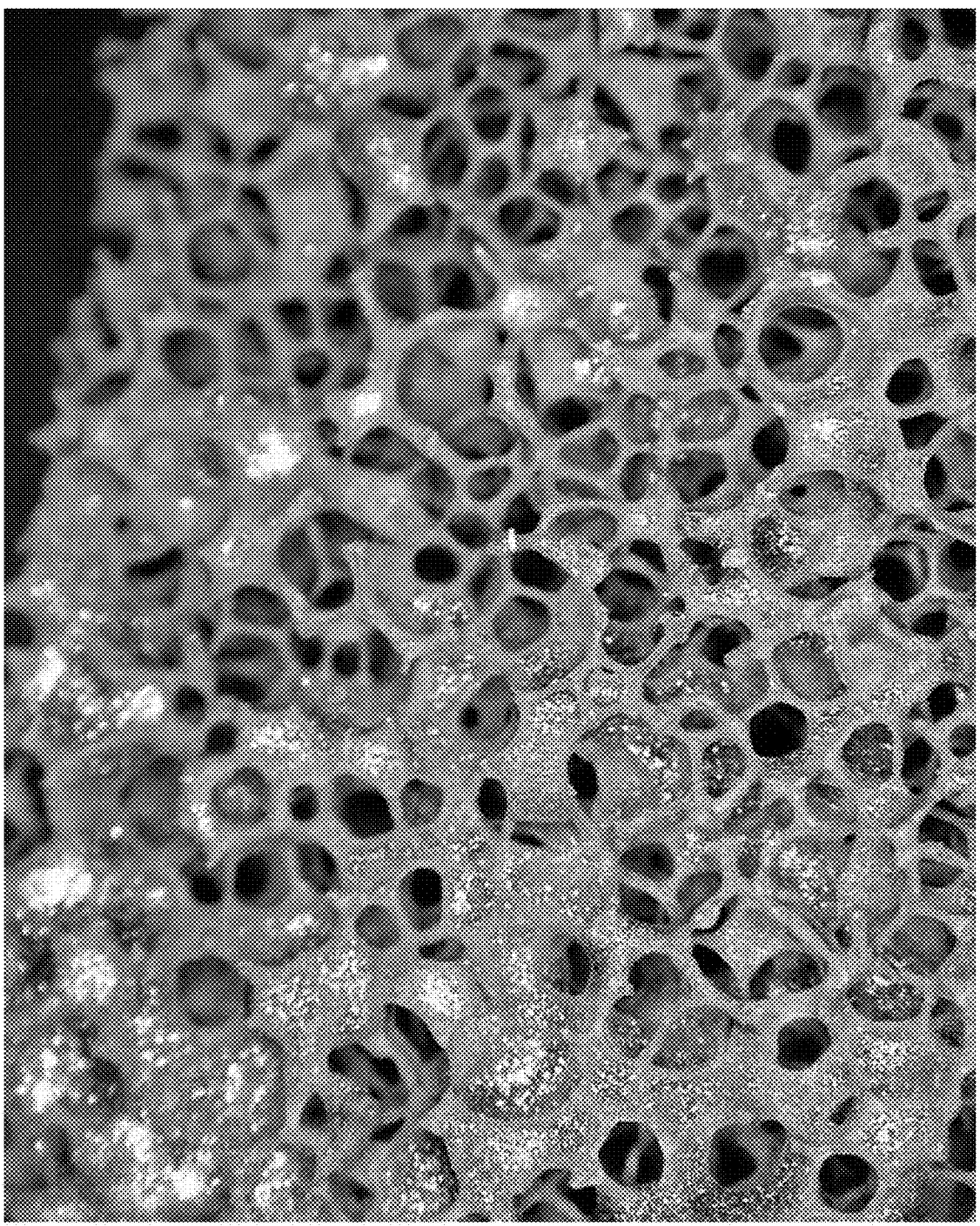
FIG. 16. Photograph of one embodiment of a porous part prepared by 3D-printing.
Figure 17:
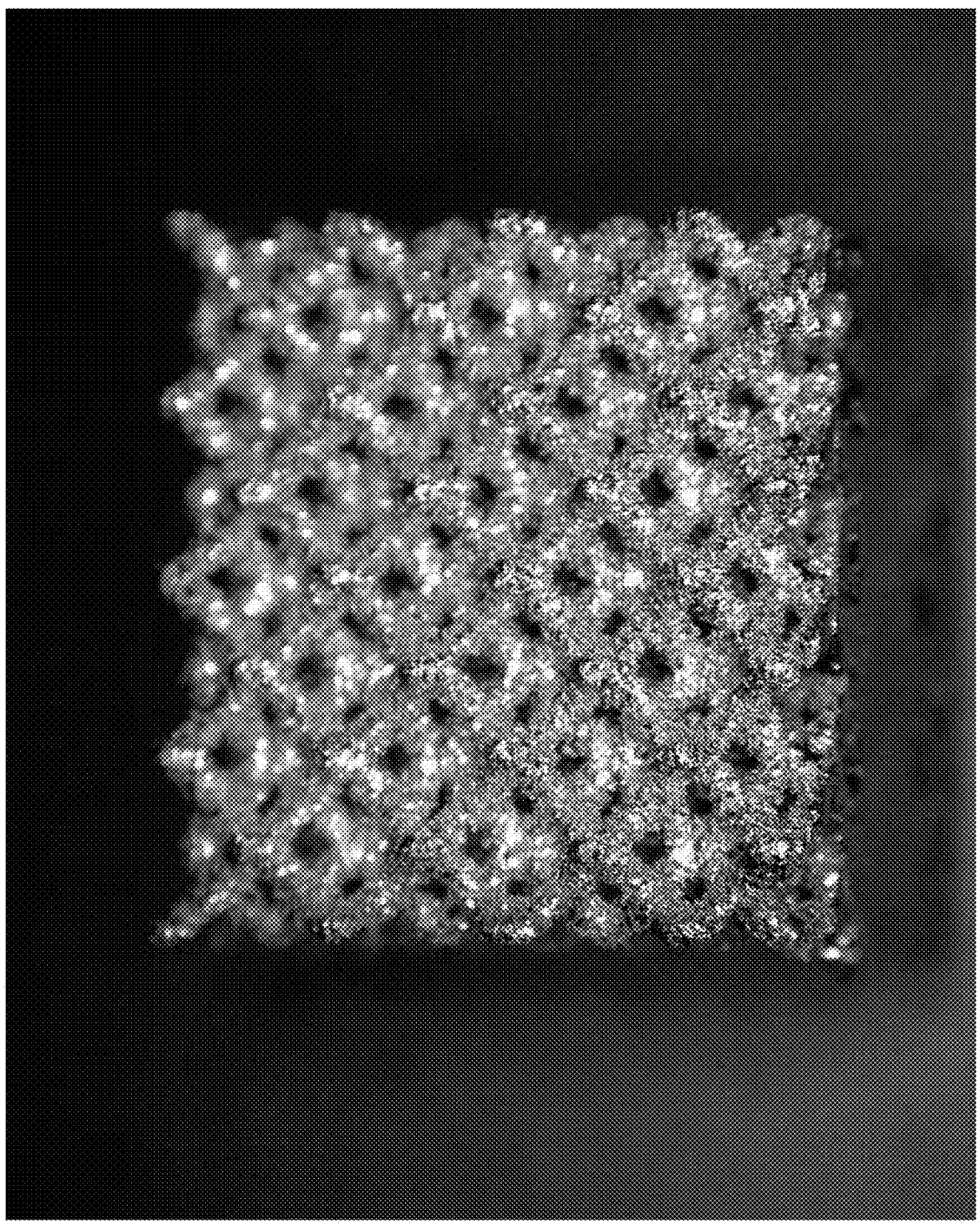
FIG. 17. Photograph of one embodiment of a porous part prepared by microsphere sintering.
Figure 18:
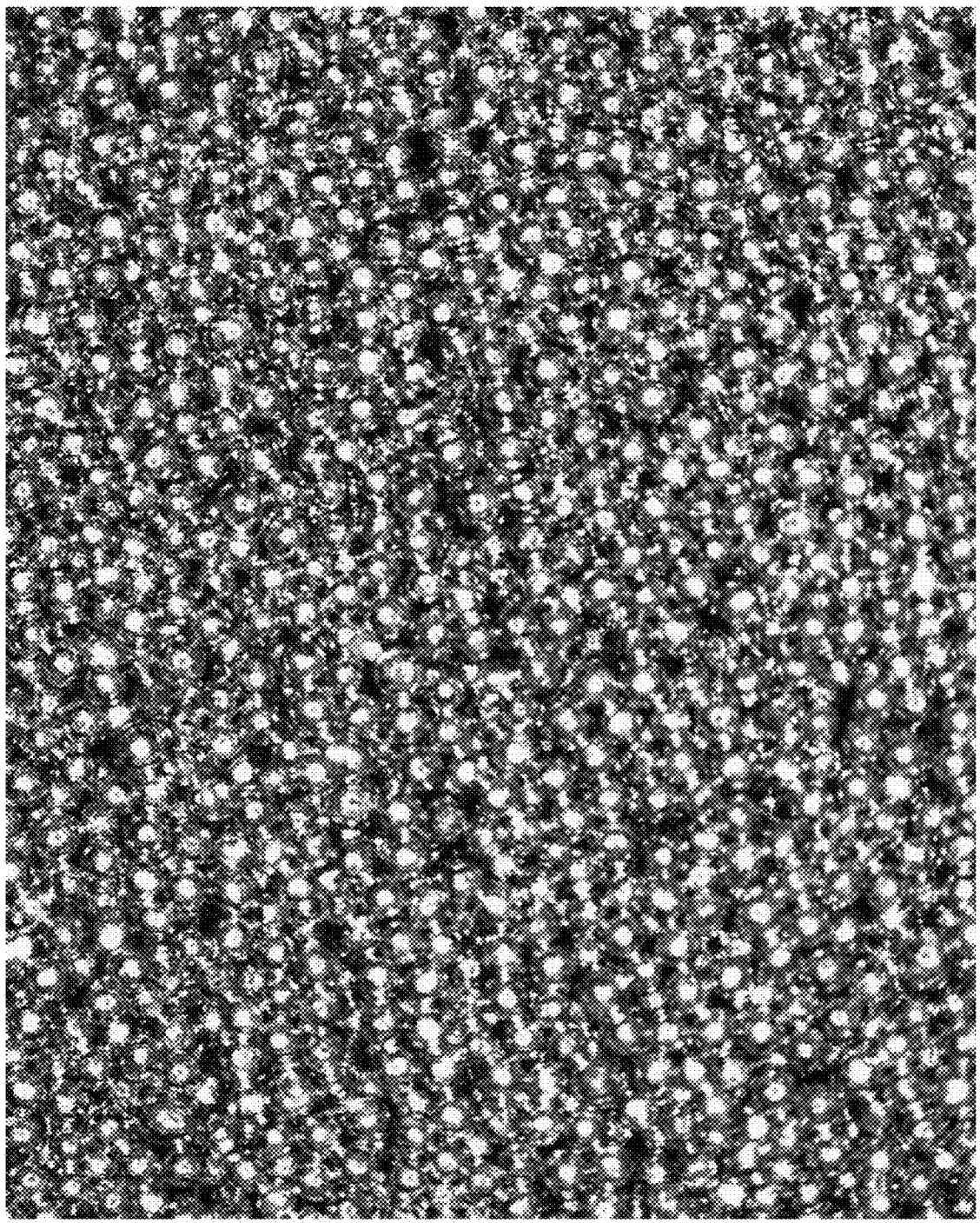
FIG. 18. Photograph of one embodiment of a porous part prepared by particle sintering.

The porous part of the synthetic devices disclosed herein may be prepared by methods including but not limited to replica template/replication, 3D-printing, microsphere sintering, particle sintering, powder sintering, fiber sintering, gas injection into the metal melt, decomposition of foaming agents, plasma spraying, space holder method, combustion synthesis, vapor deposition, and electro discharge compaction. FIG. 15 provides a photograph of a porous part prepared by replica template/replication. FIG. 16 provides a photograph of a porous part prepared by 3D-printing. FIG. 17 provides a photograph of a porous part prepared by microsphere sintering. FIG. 18 provides a photograph of a porous part prepared by particle sintering.

In some embodiments of the disclosed synthetic prosthesis, the porous part facilitates bio-integration of the prosthesis (e.g., into an eye of a patient).

In some embodiments of the disclosed synthetic prosthesis, the solid part may comprise or may be made of metals. In particular, the solid part may comprise or may be made of titanium or titanium alloys (e.g., Ti-6Al-4V alloy).

In some embodiments of the disclosed synthetic prosthesis, the solid part may comprise or may be made of ceramics. In particular, the solid part may comprise or made be made of hydroxyapatite, tri-calcium phosphate.

In some embodiments of the disclosed synthetic prosthesis, the solid part may comprise or may be made of a polymeric material. In particular, the solid part may comprise or may be made of poly(methyl methacrylate) (PMMA) and/or polyethylene material.

In some embodiments of the disclosed synthetic prosthesis, the solid part may comprise or may be made of a composite comprising a combination of any of metal (or metal alloy) material, ceramic material, and/or polymeric material as contemplated herein.

In some embodiments of the disclosed synthetic prosthesis, the solid part may be coated or treated using any of metal (or metal alloy) material, ceramic material, polymeric material, hydrogel materials, and/or a composite comprising a combination of any of metal (or metal alloy) material, ceramic material, hydrogel materials, and/or polymeric material as contemplated herein.

The disclosed synthetic prosthesis typically includes a hole made through the porous part and the solid part. The diameter of the hole might be the same or different through the porous part and the solid part. In some embodiments of the disclosed synthetic prosthesis, the hole has a diameter from 1 to 8 mm, preferably 2-6 mm, more preferably 3-5 mm.

In some embodiments of the disclosed synthetic prosthesis, the hole is substantially centered in the prosthesis through the porous part and the solid part. In other embodiments of the disclosed synthetic prosthesis, the hole may deviate from the center of the porous part and/or the solid part.

REFERENCES

[1] Strampelli B. Keratoprosthesis with osteodontal tissue. Am J Ophthalmol 1963; 89:39.
[2] Liu C, Paul B, Tandon R, Lee E, Fong K, Mavrikakis I, et al. The osteo-odonto-keratoprosthesis (OOKP). Seminars in ophthalmology: Taylor & Francis; 2005. p. 113-28.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A synthetic keratoprosthesis for use in eye surgery, the synthetic keratoprosthesis comprising:
   a porous part, a solid non-porous part attached to the porous part, and a hole through the porous part and the solid non-porous part configured for receiving an optical cylinder; and
   an optical cylinder placed in the hole of the synthetic keratoprosthesis,
   wherein the porous part and solid non-porous part are laminate parts,
   wherein dimensions of the porous part and the solid non-porous part are the same in width and depth, and different in height,
   wherein the porous part and the solid non-porous part form a rectangular cuboid.

2. The synthetic keratoprosthesis of claim 1, wherein the porous part and the solid non-porous part of the synthetic keratoprosthesis are permanently attached.

3. The synthetic keratoprosthesis of claim 1, wherein the porous part and the solid non-porous part of the synthetic keratoprosthesis are removably attached.

4. The synthetic keratoprosthesis of claim 1, wherein the porous part and the solid non-porous part comprise the same material or different materials selected from metal material, ceramic material, polymeric material, or a composite comprising any combination of metal material, ceramic material, and polymeric material.

5. The synthetic keratoprosthesis of claim 1, wherein the porous part and the solid non-porous part are coated using the same material or different materials selected from metal material, ceramic material, polymeric material, or a composite comprising any combination of metal material, ceramic material, and polymeric material.

6. The synthetic keratoprosthesis of claim 1, wherein the Width (W) of the porous part and the solid non-porous part is the same and ranges from 2 to 20 mm, wherein the Depth (D) of the porous part and the solid non-porous part is the same and ranges from 1 to 15 mm, and wherein the Height (H) of the porous part and the solid non-porous part is different and ranges from 0.1 to 5 mm.

7. The synthetic keratoprosthesis of claim 6, wherein the width (W) of the solid non-porous part and the porous part ranges from 6-16 mm, wherein the Depth (D) of the solid non-porous part and the porous part ranges from 4-12 mm, and wherein the Height (H) of the solid non-porous part ranges from 0.25-2 mm, and wherein the Height (H) of the porous part ranges from 0.5-2.5 mm.

8. The synthetic keratoprosthesis of claim 1, wherein the porous part comprises a coating, wherein the coating comprises any of metal material, ceramic material, polymeric material and/or a composite comprising a combination of any of metal material, ceramic material, and/or polymeric material.

9. The synthetic keratoprosthesis of claim 1, wherein the porous part comprises pores having an average effective pore size of 10 to 1000 microns.

10. The synthetic keratoprosthesis of claim 1, wherein the porous part has a volumetric porosity of 10 to 95%.

11. The synthetic keratoprosthesis of claim 1, wherein the porous part and the solid non-porous part comprise titanium or titanium alloy.

12. The synthetic keratoprosthesis of claim 1, wherein the solid non-porous part comprise a coating, wherein the coating comprises any of metal material, ceramic material, polymeric material and/or a composite comprising a combination of any of metal material, ceramic material, and/or polymeric material.

13. The synthetic keratoprosthesis of claim 1, wherein the diameter of the hole through the keratoprosthesis has a diameter that is the same through the porous part as through the solid non-porous part.

14. The synthetic keratoprosthesis of claim 1, wherein the diameter of the hole through the keratoprosthesis has a diameter that is different through the porous part than through the solid non-porous part.

15. The synthetic keratoprosthesis of claim 1, wherein the hole has a diameter from 1 to 8 mm.

16. The synthetic keratoprosthesis of claim 1, wherein the optical cylinder comprises poly(methyl methacrylate) (PMMA) and/or polyethylene material.

* * * * *